United States Patent [19]
Arichi et al.

[11] 4,352,796
[45] Oct. 5, 1982

[54] PHARMACEUTICALLY ACTIVE PLANT EXTRACT AND COMPOSITION THEREOF

[75] Inventors: Shigeru Arichi; Yoshihiro Uchida, both of Osaka, Japan

[73] Assignee: Osaka Chemical Laboratory Co., Ltd., Osaka, Japan

[21] Appl. No.: 158,598

[22] Filed: Jun. 11, 1980

[30] Foreign Application Priority Data

Jun. 14, 1979 [JP] Japan .................................. 54/75349

[51] Int. Cl.$^3$ ............................................. A61K 35/78
[52] U.S. Cl. .................................................... 424/195
[58] Field of Search ........................................ 424/195

[56] References Cited
PUBLICATIONS

Biol. Abstracts 68(10): 62835; 68(9): 55978; 67(9): 56888.
Chem. Abstracts 91: 49432K citing J. Pharmacolo-Gyn., 1979, 2(2); 78–83, currently not available.

*Primary Examiner*—Donald B. Moyer
*Attorney, Agent, or Firm*—Hubbell, Cohen, Stiefel & Gross

[57] ABSTRACT

There discloses a substantially alkaloid-free aqueous extract of an aconite root which is the dried tuberous root of *Aconitum japonicum* or like plant belonging to Ranunculaceae, which is useful as analgesic and antiphlogistic.

9 Claims, 3 Drawing Figures

PHARMACEUTICALLY ACTIVE PLANT EXTRACT AND COMPOSITION THEREOF

BACKGROUND OF THE INVENTION

1. Field of the Invention

This invention relates to a pharmaceutically active plant extract and composition thereof. More particularly, this invention is concerned with a process for preparing a substantially alkaloid-free aqueous or dry extract from an aconite root, i.e., a root of *Aconitum japonicum* Thunberg or any other like-plant belonging to the genus Aconitum, the family Ranunculaceae, and pharmaceutical preparations containing such an extract.

2. Description of the Prior Art

An aconite root is the root of Aconitum plant such as *Aconitum japonicum* Thunberg or *Aconitum sinense* Siebold, and is listed in e.g. the 7th Revision of the Japanese Pharmacopoeia. It has long been known that the aconite root is useful as a cardiotonic, analgesic or antiphlogistic, and is also effective for retarding ageing and invigoration by promoting the metabolism. A crude drug prepared from it is used internally in the form of powder or a decoction, and on rare occasions, the crude drug in powder form is applied externally for relieving neuralgia and rheumatism. As is obvious from the fact that the Ainu race applies it to the arrows when hunting bears, this crude drug is highly poisonous, and can often cause anesthesia leading to death if used in a wrong quantity. The toxicity of the drug is due to a dozen or so alkaloids contained in the aconite root, such as aconitine ($C_{34}H_{47}O_{11}N$), mesaconitine ($C_{33}H_{45}O_{11}N$), hypaconitine ($C_{33}H_{45}O_{10}N$) and atisine ($C_{22}H_{33}O_2N$). Aconitine is present in a greater quantity than any other alkaloid, and is so toxic that a man will die if he takes 3 or 4 mg of aconitine. The cardiotonic, analgesic and antiphlogistic actions of the aconite root have hitherto been attributed to its alkaloids, particularly aconitine or like alkaloids, and those formed by removing acetyl and benzoyl groups from aconitine or like alkaloids [Jiro Imai: Journal of Tokyo Medical College, 7, 1 (1949), Teijiro Agawa: Journal of Tokyo Medical College, 12, 1 (1954), and Hirohisa Goto: Journal of Jap. Soc. of Pharmacology, 52, 4 (1956)]. Accordingly, there have been proposed a number of methods for processing the aconite root to reduce its toxicity as far as possible. As it has been considered that the removal of the acetyl group from virulently poisonous aconitine converts it to benzoylaconine having a relatively low toxicity, one of those methods provides a processed aconite root prepared by heating an aconite root under pressure to convert the greater part of its aconitine into benzoylaconite (Japanese Pat. No. 406,780). Another method provides a steamed aconite root prepared by immersing an aconite root in bittern, and subjection it to prolonged steaming treatment to convert its aconitine into benzoylaconine. Benzoylaconine is, However, a poisonous alkaloid, as it shows a lethal dose of 27.2 mg/kg when injected hypodermically into a domestic animal, though it is certainly lower in toxicity than aconitine, which has a lethal dose of 0.131 mg/kg. Thus, the processed and steamed aconite roots are both specified as powerful drugs by the Minister of Public Welfare in Japan.

SUMMARY OF THE INVENTION

The inventors of this invention have for the first time discovered that the analgesic and antiphlogistic actions of an aconite root are primarily attributable to a water-soluble extract obtained by removing all the alkaloids from the aconite root. This invention eliminates all the fear involved in the toxicity of the aconite root, and enables its use in the form of a water-soluble extract, rather than a crude powder, for analgesic and antiphlogistic purposes. This invention makes it possible to dramatically expand the scope of application of the aconite root, since its water-soluble extract can be easily prepared into various dosage forms.

According to this invention, there is, thus, provided a phamaceutical composition containing as an active constituent an aqueous or dry extract of an aconite root which does not substantially contain any alkaloid. This invention also provides a process for preparing an aqueous or dry extract of an aconite root which does not substantially contain any alkaloid.

For the purpose of this invention, the aconite roots include the root of plants belonging to the genus Aconitum of the family Ranunculaceae. Concrete examples are *Aconitum japonicum* Thunberg, *A. sinense* Siebold, *A. zuccarini* Nakai, *A. Subcuneatum* Nakai, *A. aizuense* Nakai, *A. sanyoense* Nakai, *A. napéllus* Linné, *A. carmichaeli* Debeaux, *A. volubile* Pallas, *A. chinense* Paxton, *A. Fischeri* Reichenbach, *A. yesonense* Nakai, *A. Sachalinense* Fr. ScHM, *A. Koreanum* R. Raymond, *A. ferox* Wall, *A. deinorrhizum* Stapf, *A. teterophyllum* Wall, *A. palmatum* Raymond, *A. loczyanum* R. Raymond, *A. pterocaule* Koidz, *A. gigas* LEV. el VAN, *A. senanense* Nakai, *A. matsumurae* Nakai, *A. metajapanicum* Nakai, *A. nakusanense* Nakai, *A. yuparense* Takeda, *A. kusnezoffic* Reichenbach, *A. manshuricum* Nakai, *A. vilmorinianum* Kom., *A. paniculigerum* Nakai, *A. artemisaefolium* Bar. et Skv., *A. taipeicum* Hand.-Mazz., *A. stylosum* Staph, *A. Karakolicum* Rap., *A. soongarium* Stapf, *A. hemsleyanum* Pritz., *A. delavayi* Franch., *A. sungpanense* Hand.-Mazz., *A. balfourii* Stapf, *A. richardsonianum* Lauener, *A. transsectum* Diels, etc.

Preferred ones are *A. japonicum* Thurnberg and *A. sinense* Siebold. These roots are conventionally used in dried form (hereinafter stated as dried aconite root). The modified roots are also usable for the raw material of the present invention. Examples of the modifications are to subject the root to dipping in concentrated sodium chloride aqueous solution and drying; to dipping in bittern, steaming the dipped root and drying; (hereinafter stated as steamed aconite root); or to heating with water under an elevated pressure and drying (hereinafter stated as processed aconite root). Such modified aconite roots are known under names of Tenyu, Sokushi, Soo-uzu, Sen-usu, Dai-busi, Shirakawa-bushi, Hootenyu, Hoo-busi, En-busi, Kako-busi, etc.

DESCRIPTION OF THE PREFERRED EMBODIMENTS

Figure 1:
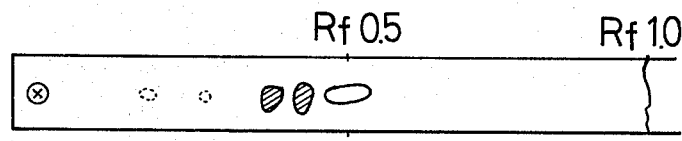
FIG. 1 shows a thin layer chromatogram for the non-alkaloidal extract of an aconite root.

The aforementioned aconite roots are generally treated by one of the following three processes for separaration of their active constituents:

PROCESS I

The aconite root is extracted with water, a lower aliphatic alcohol containing water or a lower aliphatic alcohol. The extract is concentrated or dried by evaporation, and dissolved in a weakly basic aqueous solution (e.g. of pH 8-10). The solution is extracted with a fat-soluble organic solvent unitl its water layer shows a negative alkaloidal reaction. The water layer is neutralized and concentrated to form an aqueous extract of the aconite root which is substantially free of any alkaloid. If desired, this extract is dried to form a dry extract.

PROCESS II

The aconite root is impregnated with weakly basic aqueous solution, and subjected to extraction with a fat-soluble organic solvent until it shows a negative alkaloidal reaction. The aconite root is, then, extracted with water, a lower aliphatic alcohol containing water or a lower aliphatic alcohol, and the extract obtained is concentrated to form an aqueous extract of the aconite root which is substantially free of any alkaloid. If desired, this extract is dried to form a dry extract.

PROCESS III

The aconite root is extracted with water. The extract obtained is concentrated and contacted with a cation exchange resin for removal of the alkaloids by adsorption, or alternatively, the extract which is not concentrated is contacted with a cation exchange resin, and then concentrated, whereby an aqueous extract of the aconite root which is substantially free of any alkaloid is formed. If desired, this extract is dried to form a dry extract.

Examples of the lower aliphatic alcohol for use in any of the aforementioned Processes I to III include methanol, ethanol, propanol, isopropanol, and butanol. Examples of the fat-soluble organic solvent used for alkaloid extraction include chloroform, ethyl ether, benzene, hexane, toluene, xylene, ligroin and petroleum ether.

Examples of the cation exchange resin used in Process III include strongly acidic cation exchange resins such as Amberlite ® IR-120 and Duolite ® C-10, and weakly acidic cation exchange resins such as Amberlite ® IRC-50 and Duolite ® CC-3. The extract (water impregnated aconite) can be contacted with the cation exchange resin by various methods. For example, the extract may be passed through a column filled with the cation exchange resin, or may be mixed with the resin. In the latter case, the resin is separated from the extract by filtration, or otherwise.

Whichever of the Processes I to III may be used, the concentration of the extract should preferably be carried out under reduced pressure.

A solid or liquid excipient may be added to the aqueous or dry extract prepared as described above in order to compose various dosage forms for internal or external use. The extract can also be used in the form of an injection or instillation.

External preparations may be in the form of ointments, plasters, solutions (including spirits, tinctures, and lotions), fomentations (poultices and pastes), paints, aerosols, conspergatives, suppositories, liniments (inunctions), creams, emulsions, or baths.

Internal preparations may be in the form of powders, tablets, emulsions, capsules, teas, granules, and solutions (including spirits, inctures, fluid extracts and syrups).

The solid or liquid excipient may be selected from among those known in the art. It is, however, desirable that the preparations each contain a suitable dose of the substance according to this invention.

Specific examples of the excipient for making powdered preparations for external use include zinc oxide, talc, starch, kaolin, boric acid, zinc stearate, magnesium stearate, magnesium carbonate, precipitated calcium carbonate, bismuth subgallate, and potassium aluminum sulfate. Examples of the excipient for liquid preparations include water, glycerol, propylene glycol, a single syrup, ethanol, fatty oil, ethylene glycol, polyethylene glycol, and sorbitol. The excipients for ointments may, for example, comprise a hydrophobic or hydrophilic base prepared by combining fats, fatty oils, lanolin, vaseline, glycerol, beeswax, Japan wax, paraffin, liquid paraffin, resins, higher alcohols, plastics, glycols, water and a surface active agent, including emulsion, water-soluble and suspension type bases.

Baths may be prepared by adding duluting agents, such as Glauber's salt and potassium sulfate, into the active constituents according to this invention.

Examples of the excipient for preparing powdered drugs for internal use include milk sugar, starch, dextrin, calcium phosphate, calcium carbonate, synthetic or natural aluminum silicate, magnesium oxide, desiccated aluminum hydroxide, magnesium stearate, sodium hydrogencarbonate, and dry yeast.

According to this invention, it is possible to make odorless, analgesic and antiphlogistic preparations for external use, such as poultices and liniments, as it is not necessary to use odorous constituents, such as 1-menthol and methyl salicylate.

According to this invention, the analgesic and antiphlogistic preparations for external use may contain 0.00001 to 5.0% of, preferably 0.001 to 0.1% of, a non-alkaloidal extract (dry). In the event the preparation is used in the form of a bath, it is desirable that the bath contain 0.0001 to 1.0% of the non-alkaloidal extract in water.

The dosage of an internal preparation depends on the condition of a patient, but for an adult, it is generally appropriate to administer it so that he may take 50 to 1,000 mg of, preferably 100 to 500 mg of a dry, non-alkaloidal extract a day in two or three doses.

The invention will now be described in further detail with reference to examples.

EXAMPLE 1

1 kg of steamed aconite root (which is the modified root of *A. japonicum* Thunberg which is dipped in bittern, steamed and dried) cut into small pieces were placed in 5 liters of hot water, and heated for four hours, followed by filtration. This extraction procedure was repeated twice. The filtrates obtained were put together, and concentrated to about 0.5 liter under reduced pressure at a temperature not higher than 70° C.

Aqueous ammonia was added into the concentrate to form a weakly basic solution having a pH value of 9.5. After 0.5 liter of chloroform was mixed into the solution with careful shaking, it was left stationary until an aqueous layer separates. This aqueous layer was taken out, and the same procedure was repeated two more times.

A small portion was taken out from the aqueous product obtained, and a Dragendorff reagent according to the Japanese Pharmacopoeia was added thereto to ascertain that the product was free of any alkaloid, i.e. there was no formation of any orange precipitate. Then hydrochloric acid was added into the aqueous product to neutralize it to pH 7.0, and it was concentrated under reduced pressure at a temperature not exceeding 70° C. until a soft extract having a water content of 35% was formed. Thus, 180 g of brown, soft extract was obtained. This extract was dried by concentration under reduced pressure at a temperature not exceeding 60° C. to yield 123 g of dry extract powder.

The properties of the non-alkaloidal extract thus obtained were as follows:

1. Both the soft extract and the dry extract powder had a protein like odor and a slightly bitter taste. They were each soluble in water, making it slightly turbid. They were also soluble in methanol and ethanol, but were insoluble in chloroform, benzene, petroleum ether, or ether. 2. A 1% aqueous solution of the extract was neutral.

3. 0.5 ml of the Dragendorff reagent (alkaloid reagent) was added into a aqueous solution containing 1 g of the extract in 10 ml of water, and the solution showed a negative reaction. The solution also showed a negative reaction against 0.5 ml of the Meyer's reagent.

4. An aqueous solution containing 1 g of the extract in 10 ml of water was subjected to thin layer chromatography under the following conditions:

Plate: Silica gel 60 F 254 (Merck)
Developing solvent: Mixture of chloroform, methanol and water (5:4:1)
Developing distance: 10 cm
Detection: Heating at 105° C. for three minutes after spraying a 1% cerium sulfate-10% sulfuric acid solution.

Spots appeared as shown in FIG. 1, including three distinct spots having Rf values of about 0.4, about 0.45 and about 0.5, respectively. The spot having an Rf value of about 0.5 was particularly clean. Reference is made to FIG. 1 for details of the chromatogram obtained.

An extract containing alkaloids showed at least eight orange spots between the Rf values of about 0.65 and 0.85 upon spraying of the Dragendorff reagent under the aforementioned conditions of thin layer chromatography. The extract according to this invention had no spot whatsoever formed by the Dragendorff reagent. This, and the negative reaction against the aforementioned alkaloid precipitation reagent proved the extract to be free of any alkaloid.

The lethal doses of the dry and soft extracts were tested by intraperitoneal injection into dds pure line male mice having an average weight of 20 g. The dry extract showed a $LD_{50}$ of 1.40 g/20 g, and the soft extract a $LD_{50}$ of 1.78 g/20 g, while a dried aconite root, a steamed aconite root and a processed aconite root showed lethal doses 50% of 0.004 g/20 g, 0.10 g/20 g and 0.12 g/20 g, respectively, when their aqueous decoctions were intraperitoneally injected into mice. Thus, it was found that the extracts of this invention had no toxicity to be feared.

The non-alkaloidal extracts of the aconite root prepared as described above were clinically applied in the following cases:

CASE 1

(Analgesic and antiphlogistic ointment)

An ointment was prepared by mixing uniformly 0.1 g of the soft, alkaloid-free extract of Example 1 according to this invention and 100 g of a hydrophilic ointment base according to the Japanese Pharmacopoeia. The ointment was applied once a day to the affected part of each patient having inflammation or a pain, and the affected part was left as it was, or bandaged with gauze. Each patient was examined for improvement in his or her pain and the condition of his or her disease every day for six days after the application of the ointment. The results are shown in Table 1, in which the bad condition of the patient is indicated as A, the medium condition as B, the fair condition as C and the good condition as D. The evaluation of the effect is shown as very high when the condition was improved from A to D, as high when the condition was improved from A to C, as slightly high when the condition was improved from A to B, and as low when the condition A remained unchanged.

As shown in Table 1, three of the ten patients had their conditions greatly improved on the second day after application of the ointment, and the remaining seven patients had their conditions likewise improved on the third day. Thus, the ointment showed a very high effect on all of the ten patients on whom it had been tested, in a very short time without causing any side effect at all.

TABLE 1

| Patient No. | Age | Sex | Disease | Symptoms | First exam. | 1st day | 2nd day | 3rd day | 4th day | 5th day | 6th day | Evaluation | Side effect |
|---|---|---|---|---|---|---|---|---|---|---|---|---|---|
| 1-1 | 30 | M | Cervical syndrome | Shoulder discomfort | A | C | D | D | D | D | D | Very high | — |
| 1-2 | 53 | F | Cervical syndrome | Shoulder discomfort | A | C | D | D | D | D | D | " | — |
| 1-3 | 74 | F | Low back pain | Low back pain | A | C | C | D | D | D | D | " | — |
| 1-4 | 25 | F | Cervical syndrome | Shoulder discomfort | A | C | C | D | D | D | D | " | — |
| 1-5 | 53 | M | Frozen shoulder | Shoulder joint pain | A | C | C | D | D | D | D | " | — |
| 1-6 | 67 | F | Knee arthritis | Knee joint pain | A | C | C | D | D | D | D | " | — |
| 1-7 | 52 | M | Frozen shoulder | Shoulder joint pain | A | C | D | D | D | D | D | " | — |
| 1-8 | 37 | F | Low back pain | Low back pain | A | C | C | D | D | D | D | " | — |
| 1-9 | 53 | F | Knee arthritis | Knee joint pain | A | C | C | D | D | D | D | " | — |
| 1-10 | 44 | M | Sciatica | Femoral low back pain | A | C | C | D | D | D | D | " | — |

CASE 2

(Analgesic and antiphlogistic poultice)

As the application of the ointment containing 0.1% of the extract of Example 1 had produced a very high effect on all of the patients tested, a poultice was tested for efficacy when containing 0.01% of the extract. The poultice was prepared by kneading 0.01 g of the soft, alkaloid-free extract of the aconite root and 100 g of a poultice base uniformly. It was applied twice a day to the affected part of each patient tested, and the improvement of his or her condition was observed every day for seven days, starting on the day on which the first examination had been made, as had been done in Case 1. The results are shown in Table 2, in which the condition of the disease and the evaluation of the improvement are indicated as described in connection with Case 1.

As shown in Table 2, the poultice produced a very high effect on seven of the ten patients, a high effect on two patients, and a slightly high effect on the remaining one patient during the seven days of the treatment. These clinical results evidence the rapid action of the alkaloid-free extract of the aconite root according to this invention.

tract was dried by concentration under reduced pressure at a temperature not exceeding 60° C., whereby 116 g of dry extract powder were obtained.

EXAMPLE 3

1 kg of steamed aconite roots (of *A. japonicum* Thunberg) cut into small pieces were heated for four hours with 5 liters of 50% methanol, followed by filtration. This extraction procedure was repeated twice. The filtrates thereby obtained were combined, and dried by concentration under reduced pressure at a temperature not exceeding 70° C. The concentration residue was dissolved in 0.5 liter of water with careful stirring, and the insoluble was removed by filtration. Aqueous ammonia was added into the substrate to form a weakly acidic solution having a pH value of 9.5. After 0.5 liter of chloroform was added into the solution with careful shaking, the solution was left stationary to separate an aqueous layer. This chloroform treatment was repeated until no orange precipitate was formed in the aqueous layer upon addition of the Dragendorff reagent, indicating that all the alkaloids were removed. Then, the aqueous product was neutralized with hydrochloric acid, and concentrated at a temperature not exceeding 70° C. to yield 145 g of a soft extract having a water content of 35%. This extract was dried by concentration under reduced pressure at a temperature not exceeding 60° C., whereby 108 g of dry extract powder were obtained.

TABLE 2

| Patient No. | Age | Sex | Disease | Symptoms | First exam. | 1st day | 2nd day | 3rd day | 4th day | 5th day | 6th day | Evaluation | Side effect |
|---|---|---|---|---|---|---|---|---|---|---|---|---|---|
| 2-1 | 40 | M | Low back pain | Low back pain | A | C | C | C | D | D | D | Very high | — |
| 2-2 | 51 | F | Cervical syndrome | Shoulder discomfort | A | C | D | D | D | D | D | " | — |
| 2-3 | 34 | M | Cervical syndrome | Shoulder discomfort | A | C | C | D | D | D | D | " | — |
| 2-4 | 53 | F | Frozen shoulder | Shoulder joint pain | A | B | B | C | C | D | D | " | — |
| 2-5 | 55 | M | Frozen shoulder | Shoulder joint pain | A | A | A | B | B | C | C | High | — |
| 2-6 | 66 | F | Knee arthritis | Knee joint pain | A | B | B | B | C | D | D | Very high | — |
| 2-7 | 32 | F | Knee arthritis | Knee joint pain | A | A | B | C | D | D | D | " | — |
| 2-8 | 46 | M | Sciatica | Serious femoral low back pain | A | B | B | B | C | C | C | High | — |
| 2-9 | 37 | M | Low back pain | Low back pain | A | C | D | D | D | D | D | Very high | — |
| 2-10 | 43 | F | Frozen shoulder | Shoulder joint pain | A | A | A | A | B | B | B | Slightly high | — |

EXAMPLE 2

1 kg of steamed aconite root (of *A. japonicum* Thunberg) cut into small pieces were heated for four hours with 5 liters of methanol, followed by filtration. This extraction procedure was repeated twice. The filtrates thereby obtained were combined, and dried by concentration under reduced pressure at a temperature not exceeding 60° C. The concentrate was dissolved in 0.5 ml of water with careful stirring, and the insoluble was removed by filtration. Aqueous ammonia was added into the filtrate to form a weakly basic solution having a pH value of 9.5. After 0.5 liter of chloroform was mixed into the solution with careful shaking, the solution was left stationary to separate an aqueous layer. This chloroform treatment was repeated until no orange precipitate was formed in the aqueous layer upon addition of the Dragendorff reagent, so that all the alkaloids were removed. Then, the aqueous product was neutralized with hydrochloric acid to pH 7, and concentrated at a temperature not exceeding 70° C. to yield 162 g of a soft, brown, alkaloid-free extract of the aconite root having a water content of 35%. This extract was dried by concentration under reduced pressure at a temperature not exceeding 60° C.,

EXAMPLE 4

1 kg of aconite root powder (of *A. sinense* Siebolt) was placed in 100 ml of 5% aqueous ammonia, and stirred carefully, so that the powder might be uniformly impregnated with aqueous ammonia. The solution was heated for two hours with 5 liters of ether, followed by filtration. This extraction procedure was repeated until no alkaloid was detected in the ether extract with the Dragendorff reagent. After all the alkaloids were removed from the aconite root powder, it was dried at 40° C. until it did not have any odor of ether or ammonia any more. The alkaloid-free powder was placed in 5 liters of hot water, and heated for four hours, followed by filtration. This extraction procedure was repeated two more times. The filtrates thereby obtained were combined, and concentrated under reduced pressure at a temperature not exceeding 70° C. to yield 184 g of a soft, brown, alkaloid-free extract of the aconite root having a water content of 35%. This extract was dried under reduced pressure at a temperature not exceeding 60° C. to yield 125 g of dry extract powder.

EXAMPLE 5

1 kg of steamed aconite roots (of *A. japonicum* Thunberg) cut into small pieces were heated for four hours with 5 liters of hot water, followed by filtration. This extraction procedure was repeated twice, and the filtrates thereby obtained were combined. The combined filtrate was caused to pass at a flow rate of 50 ml per minute through an ion exchange column filled with 5 liters of a strongly acidic cation exchange resin Amberlite IR-120 converted to H-type, whereby the alkaloids were adsorbed by the resin. Downstream of the column, the filtrate was caused to flow through 5 liters of purified water, and washed thereby. The filtrate was collected, and concentrated under reduced pressure at a temperature not exceeding 70° C. to yield 178 g of a soft, brown, alkaloid-free extract of the aconite root having a water content of 35%. This extract was dried under reduced pressure to yield 127.4 g of dry extract powder.

All the extracts prepared as described in Examples 2 to 5 showed the same physical properties as the product of Example 1.

Attention is now directed to examples of the pharmacological tests conducted by using male rats of the Wistar line to ascertain the analgesic and antiphlogistic actions of the alkaloid-free extracts according to this invention. All the dosages of the extracts were based on the dry weight. The rats had a weight of 130 to 150 g, and were divided into groups of six.

A. PHARMACOLOGICAL TESTS ON ANTIPHLOGISTIC ACTION

1. Adjuvant Arthritis-Anderson Method

[Method]

0.1 ml of Freund's complete adjuvant was hypodermically injected into the sole of the right hind foot of each rat to cause swelling therein. 300 mg/kg of the extract of Example 1 was orally administered to the rats belonging to a first group every day beginning on the day on which the injection had been given. No such extract was given to the rats belonging to a second or control group. The rats belonging to a third group were orally given 50 mg/kg of phenylbutazone as an antiphlogistic for the purpose of comparison with this invention. The plantar swelling of each rat was measured every other day until eleven days after the injection had been given. The measurement was carried out by immersing the foot of each rat in mercury, and recording the volume of its swelling electrically through a transducer. The rates of swelling were compared between the first group and the second or control group in order to obtain the rate of inhibition by the alkaloid-free extract applied to the first group. The rate of swelling for each rat was calculated as follows:

$$\text{Rate of swelling (\%)} = \frac{Vt - Vn}{Vn} \times 100$$

wherein $Vn$ stands for the normal plantar volume which the rat had before the injection of the adjuvant, and $Vt$ stands for its plantar volume after the injection.

[Test Results]

Figure 2:
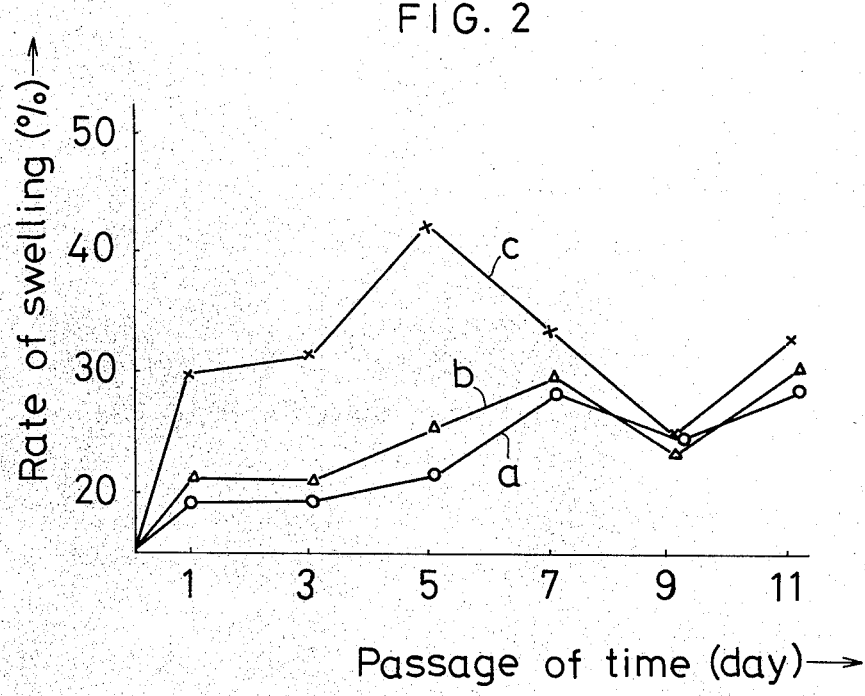
FIG. 2 is a graph showing daily changes in the rate of dropsical swelling as ascertained by the adjuvant arthritis-Anderson method, a: the extract of Example 1, b: phenylbutazone, c: control.

As shown in FIG. 2, the rats of the first group showed a lower rate of swelling than those of the other two groups, and achieved a swelling inhibition rate of 49.3% as compared with the control group on the fifth day of the test period on which the rats generally showed the highest rate of swelling. Throughout the entire test period, the application of the extract according to this invention at the rate of 300 mg/kg produced a somewhat better result than the dosage at the rate of 50 mg/kg of phenylbutazone presently well known as an antiphlogistic. These test results clearly testify the antiphlogistic action of the extract according to this invention.

2. EVANS BLUE DIFFUSION METHOD FOR CAPILLARY FRAGILITY TESTS

[Method]

If Trypan Blue, coloring matter, is injected into blood, it oozes out of the capillaries and colors the skin. If there is any region where inflammation has lowered the resistance of the capillaries, the skin in that region is colored more clearly. Accordingly, it is possible to determine the degree of inflammation by measuring the surface area of the skin colored in blue.

100 mg/kg of an alkaloid-free extract of Example 1 was dissolved in a physiological saline solution, and injected hypodermically into a first group of six rats. No such injection was given to a second or control group of rats. After one hour, the hair was removed from the back of each rat, and 0.1 ml of a 0.3% carragheenin physiological saline solution was injected as an inflaming agent into the back of the rat, followed by intravenous injection of 0.5 ml of 2% Evans Blue into the tail. After one hour, the total blue-colored surface areas of both the first and control groups were measured, and the rate of inhibition by the alkaloid-free extract against inflammation was calculated.

[Test Results]

As shown in Table 3 below, the first group of rats had a total surface area of $46.2\pm5.9$ mm$^2$ colored in blue, while the rats of the control group had a total surface area of $94.9\pm8.7$ mm$^2$ colored in blue. Thus, the alkaloid-free extract showed a rate of inhibition which was as high as 51.3%. These results clearly demonstrate the antiphlogistic action of the extract according to this invention.

TABLE 3

| Test group | Dosage | Blue colored surface area (mm$^2$) | Rate of inhibition (%) |
|---|---|---|---|
| Control | — | 94.9 ± 8.7 | — |
| Invention | 100 mg/kg | 46.2 ± 5.9 | 51.3 |

($p < 0.05$; n = 6)

3. COTTON PELLET METHOD FOR GRANULOMA FORMATION

[Method]

After its hair was removed, the back of each rat was slightly etherized, and incised along a short line which was perpendicular to the centerline thereof. A pair of passages leading to the axillas were cut open with a pincette, and a sterilized cotton pellet weighing 50±3 mg was implanted in each of the passages on both sides of the back. The edges of the incision were fastened with a suturing needle, and treated with penicillin. The alkaloid-free extract of Example 1 was orally administered every day for seven days beginning on the day of the implantation. On the eighth day, each rat was killed, and the granulation tissues surrounding the cotton pellets were severed from the normal tissues. The wet weight of those granulation tissues was measured, and compared with that of the granulation tissues taken from a control group of rats to which no alkaloid-free extract had been administered, whereby the rate of inhibition by the extract was calculated. 20 mg/kg of cortisone were administered to a third group of rats for comparison purposes.

[Test Results]

Figure 3:
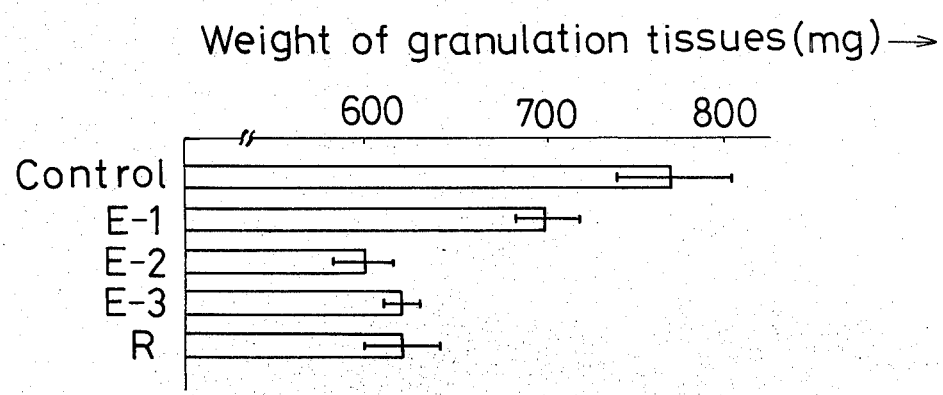
FIG. 3 is a graph showing the weight of the granulation tissue formed under various test conditions during the tests conducted by the cotton pellet method. E-1, E-2 and E-3 are the administration of 10 mg, 30 mg or 300 mg/kg of the extract of Example 1. E-4 is the administration of 20 mg/kg of cortisone.

FIG. 3 shows the average weight of the granulation tissues of each group of rats. When the granulation in the first group of rats is compared with that in the control group, the rate of inhibition by the alkaloid-free extract against granulation somewhat differs with the amount of the extract administered. The dosage of 10 mg/kg showed an inhibition rate of 11.0%, the dosage of 30 mg/kg an inhibition rate of 28.3%, and the dosage of 300 mg/kg an inhibition rate of 23.9%. The administration of 30 mg/kg of the alkaloid-free extract showed a higher rate of inhibition than 20 mg/kg of cortisone.

These test results clearly testify the antiphlogistic action of the extract according to this invention.

B. PHARMACOLOGICAL TESTS ON ANALGESIC ACTION

Pressure Stimulating Method

According to this method, the analgesic to be tested is injected into a first group of rats before the injection of an inflaming agent, while no such analgesic is injected into a second or control group of rats. After the injection of the inflaming agent, a weight is loaded on the inflamed part of the rat every hour for four hours, and when the rat feels a pain and moves its legs violently, the load thereon is measured by the Randall-Selitto method. The load is compared with that applied on the control group of rats, whereby the rate of pain relief by the analgesic is calculated.

50 mg/kg of the alkaloid-free extract were dissolved in a physiological saline solution, and injected hypodermically into the plantar part of the right hind leg of each rat of a first group. After one hour, 0.1 ml of a 1% yeast physiological saline solution was injected as an inflaming agent, followed by another hypodermic injection of 50 mg/kg of the alkaloid-free extract. After one hour, a weight was loaded on the affected part of the rat, and when it felt a pain and moved its legs, the load thereon was measured by the aforementioned method. This measurement was carried out every hour until four hours passed. The data obtained were compared with the results likewise obtained for the control group of rats, whereby the analgesic effect of the alkaloid-free extract was determined.

[Test Results]

Table 4 illustrates the analgesic effect of the alkaloid-free extract by comparing the loads at which the rats of the first and control groups complained of a pain on their affected parts after one hour, two hours, three hours and four hours following the injection of the inflaming agent.

TABLE 4

| | Lapse of time after injection of the inflaming agent | | | | |
|---|---|---|---|---|---|
| | Immediately | 1 hour | 2 hours | 3 hours | 4 hours |
| First group (Invention) | 94 g | 105 g | 96 g | 78 g | 54 g |
| Control group | 100 g | 82 g | 63 g | 49 g | 43 g |

TABLE 4-continued

| | Lapse of time after injection of the inflaming agent | | | | |
|---|---|---|---|---|---|
| | Immediately | 1 hour | 2 hours | 3 hours | 4 hours |
| Load difference | −6 g | 23 g | 33 g | 29 g | 11 g |

It is obvious from the results shown in Table 4 that the extract according to this invention has an analgesic effect. According to the test results, the first group of the rats could endure a 28% heavier load than the control group one hour after the injection of the inflaming agent, a 52.38% heavier load after two hours, a 59.18% heavier load after three hours, and a 25.58% heavier load after four hours, without feeling any pain. These results clearly demonstrate the analgesic action of the extract according to this invention.

Further, the alkaloid-free extract of this invention is also useful as an agent for promoting absorption of drugs.

For example, insulin which is a famous medicine for diabetic is used in the form of injection only, since it's oral administration is known to be ineffective. Now, it was surprisingly found that when insulin was used together with the extract of the invention in the form of suppository, it was very effective for lowering level of blood-sugar. It is believed that such fact depends upon the action of the extract to promote absorption of insulin in intestinal tract.

What is claimed is:

1. A substantially alkaloid free aqueous extract of a steamed or powdered aconite root selected from the group consisting of *Aconitum japonicum* Thunberg or *Aconitum sinense* Siebold prepared by the process comprising:
    (a) extracting said aconite root with water, a lower aliphatic alcohol containing water, or a lower aliphatic alcohol to form an extract of said aconite root;
    (b) concentrating said extract or drying it by evaporation under reduced pressure;
    (c) dissolving said extract in a slightly basic aqueous solution;
    (d) treating said aqueous solution with a fat soluble organic solvent selected from the group consisting of chloroform, ethylether, benzene, hexane, toluene, ligroin and petroleum ether until the resulting aqueous solution shows a negative reaction against an alkaloid detecting reagent, thereby removing alkaloids;
    (e) neutralizing said aqueous solution; and
    (f) concentrating said aqueous solution as in step (b), whereby a substantially alkaloid-free aqueous extract of said aconite root is obtained.

2. A substantially alkaloid-free aqueous extract of a steamed or powdered aconite root selected from the group consisting of *Aconitum japonicum* Thunberg or *Aconitum sinense* Siebold prepared by the process comprising:
    (a) impregnating said aconite root with slightly basic water;
    (b) treating said aconite root with a fat soluble organic solvent selected from the group consisting of chloroform, ethylether, benzene, hexane, toluene, ligroin and petroleum ether until said aconite root shows a negative reaction against an alkaloid detecting reagent, in order to remove alkaloids;

(c) extracting said aconite root with water, a lower aliphatic alcohol containing water, or a lower aliphatic alcohol to form an extract of said aconite root; and
(d) concentrating said extract, whereby a substantially alkaloid free aqueous extract of said aconite root is obtained.

3. A substantially alkaloid free aqueous extract of a steamed or powdered aconite root selected from the group consisting of *Aconitum japonitum* japonicum Thunberg or *Aconitum sinense* Siebold prepared by the process comprising:
(a) extracting said aconite root with water;
(b) contacting said extract or concentrate thereof with a cation exchange resin in order to absorb alkaloids thereupon; and
(c) concentrating the eluent, whereby a substantially alkaloid free aqueous extract of said aconite root is obtained.

4. The substantially alkaloid free extract according to any of claims 1, 2 or 3, wherein the extract is dryed so as to form a dry extract.

5. The substantially alkaloid free extract according to either claim 1 or 2, wherein the lower aliphatic alcohol is selected from a group consisting of methanol, propanol, isopropanol and butanol.

6. The substantially alkaloid free extract according to claim 5, wherein the lower aliphatic alcohol is methanol.

7. The substantially alkaloid free extract according to either claim 1 or 2, wherein the fat soluble organic solvent is chloroform.

8. The substantially alkaloid free extract according to claim 3, wherein the cation exchange resin is a strongly acidic cation exchange resin.

9. A method of reducing pain or inflammation in a human being comprising administering an effective amount of the extract of any of claims 1, 2 or 3.

* * * * *